United States Patent [19]

Gramatte et al.

[11] Patent Number: 5,331,843

[45] Date of Patent: Jul. 26, 1994

[54] CAPILLARY VISCOMETER APPARATUS FOR AN UNCOMPLICATED DETERMINATION OF FLOW CHARACTERISTICS OF FLUENT MATERIALS

[75] Inventors: Horst Gramatte, Rödern; Roland Worlitsch; Tim Haake, both of Medingen, all of Fed. Rep. of Germany

[73] Assignee: Haake Medingen GmbH, Medingen, Fed. Rep. of Germany

[21] Appl. No.: 67,071

[22] Filed: May 26, 1993

[30] Foreign Application Priority Data

Jun. 3, 1992 [DE] Fed. Rep. of Germany ....... 4218284

[51] Int. Cl.⁵ .......................................... G01N 11/02
[52] U.S. Cl. .................................... 73/54.09; 73/54.06
[58] Field of Search ................. 73/54.04, 54.05, 54.06, 73/54.09, 54.14

[56] References Cited

U.S. PATENT DOCUMENTS

| | | | |
|---|---|---|---|
| 3,938,369 | 2/1976 | de Bok | 73/55 |
| 4,539,837 | 9/1985 | Barnaby | 73/55 |
| 4,587,837 | 5/1986 | Newbould | 73/56 |
| 4,677,844 | 7/1987 | Sonoda | 73/55 |
| 4,680,958 | 7/1987 | Ruelle et al. | 73/56 |
| 4,793,174 | 12/1988 | Yau | 73/55 |
| 5,209,107 | 5/1993 | Grudzien, Jr. et al. | 73/54.14 |

FOREIGN PATENT DOCUMENTS

| | | |
|---|---|---|
| 2913652 | 10/1980 | Fed. Rep. of Germany . |
| 3237130A1 | 4/1984 | Fed. Rep. of Germany . |
| 3331659A1 | 4/1985 | Fed. Rep. of Germany . |
| 22371 | 7/1991 | Fed. Rep. of Germany . |
| 90013925 | 9/1984 | U.S.S.R. . |

Primary Examiner—Nina Bhat
Attorney, Agent, or Firm—Griffin Butler Whisenhunt & Kurtossy

[57] ABSTRACT

A capillary viscometer apparatus comprises a measuring cylinder (3) having an axially-movable piston (2) which is moved by a drive (1). The measuring cylinder (3) and the piston (2) define a measuring space (4) which communicates with a capillary tube or bundle (6) and a differential pressure gauge (7). A pressure difference between the measuring space (4) and a tested medium (12) is registered and processed by a signal-processing unit (9). A speed of the piston (2) is determined by means of a displacement-time measuring device or a speed measuring device (8) and this information is then transmitted to the signal-processing unit (9).

12 Claims, 3 Drawing Sheets

CAPILLARY VISCOMETER APPARATUS FOR AN UNCOMPLICATED DETERMINATION OF FLOW CHARACTERISTICS OF FLUENT MATERIALS

BACKGROUND OF THE INVENTION

This invention relates to an apparatus for determining flow characteristics of Newtonian and non-Newtonian fluids which can be used even at high temperatures and high pressures, independently of flow conditions, with materials high in sol id matter, because of its uncomplicated and sturdy construction; and which can also be used with materials which tend to coagulate, solidify, or crust, because of its self-cleaning action.

Falling ball, or sphere, viscometers, rotation viscometers, oscillation viscometers and capillary viscometers are known from prior art for determining flow characteristics.

Falling sphere viscometers can produce exact viscosity values only for Newtonian fluids, they measure only in a discontinuous manner and they cannot be used in high temperatures, under high pressures and in manufacturing processes.

Rotation viscometers can also measure non-Newtonian fluids. However, they fail when measuring tested substances which tend to settle or solidify or have high solid matter content. Further, with highly volatile fluids, an open surface negatively influences any measured results. Under processing conditions, their measured results are dependent upon flow conditions; thus, using them for testing different substances is possible only to a limited degree and can be accomplished only by interfering with viscometer flow. Particular problems arise at high pressures.

Oscillation viscometers do not involve a viscometer flow, with inertia-reaction forces and surrounding conditions not allowing exact viscosity measurements. Thus, only relative values are determined. An oscillation viscometer is not suitable for fluids which form sediments or which contain solid matter.

Prior-art capillary viscometers measure only discontinuously (e.g. measuring takes place after cleaning, filling and tempering (warming or cooling) of a storage container) or continuously in a by-pass manner wherein a defined volume flow is moved along a test path with the help of a gear pump. It is a disadvantage of this arrangement that long reaction times are required and that the gear pump fails when dealing with materials which contain solid matter and which tend to stick.

A further apparatus for measuring viscosity is described in German patent document DE-OS 33 31 659. This apparatus has the following disadvantages:

A measured value is dependent upon an environmental pressure, thus devices for generating a positive or a negative pressure are required. A measuring procedure for this device can be used only in pressure-less containers and cannot be used in high temperatures or with high mechanical loads. Flow in capillaries of this apparatus is dependent upon a fill level of a fluid in a measuring container and a measuring range is limited by a maximum achievable negative pressure.

Still another operating principle is described in DE-OS 32 37 130. Use of spring-bellows capillary viscometers poses a problem in particular with fluids containing ferrite matter because they employ electric solenoids. Also, an exchange of tested substances is not ensured and flow conditions inside capillaries thereof are not stable because of an exponential time curve of a bellows stretch.

It is an object of this invention to provide an apparatus for exactly measuring flow characteristics of fluent materials in pipes, containers and receptacles independently from pressure and flow conditions as well as from mounting positions of the viscometer. An application of the device of this invention is possible even under extreme environmental, mechanical and climatic loads.

SUMMARY

According to principles of this invention, alternating movement of a viscometer piston in a measuring cylinder, forces a defined volume of tested medium to flow through a capillary tube or a capillary bundle which is located in a tested medium. A differential pressure gauge measures a pressure drop between inside and outside the measuring cylinder.

BRIEF DESCRIPTION OF THE DRAWINGS

The invention is described and explained in more detail below using the embodiments shown in the drawings. The described and drawn features, in other embodiments of the invention, can be used individually or in preferred combinations. The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

DESCRIPTION OF THE PREFERRED EMBODIMENT

Figure 1:
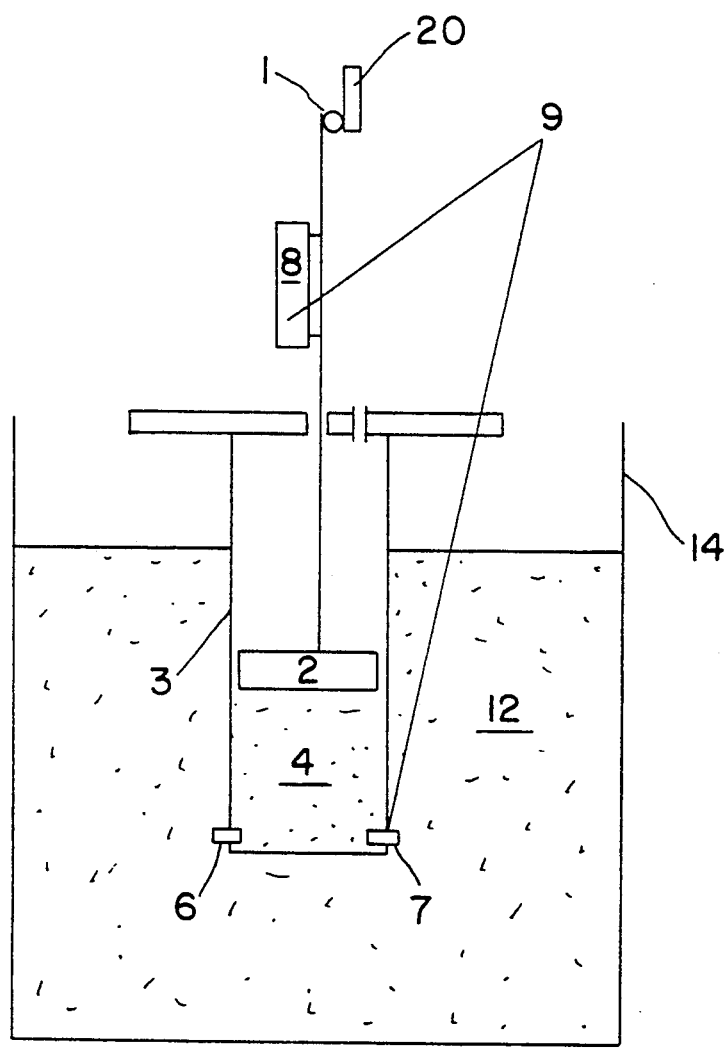
FIG. 1 is a schematic, partially cutaway, side view of a continuously measuring capillary viscometer apparatus of this invention.

FIG. 1 schematically depicts an apparatus of this invention for determining flow characteristics of fluent materials in a capillary tube 6.

A drive 1 moves a viscometer piston 2 by means of a piston rod along a predetermined test path in the interior of a measuring cylinder 3 at a constant speed in an alternating, or back-and-forth, motion. The piston 2 forms a gas-proof seal with an internal surface of the measuring cylinder 3 to define a measuring space 4. The even motion of the viscometer piston 2 in the measuring space 4 creates a constant flowing motion and thus a constant shearing speed in the interior of a capillary of the capillary tube, 6 (which could also be a capillary bundle 6A).

Depending upon the movement direction of the viscometer piston 2, a tested medium 12 is sucked in (fills) or is expelled from the measuring space 4.

A differential pressure gauge 7 measures a pressure difference between the measuring space 4 and the exterior surroundings thereof.

The capillary tube 6 and the differential pressure gauge 7 are arranged in the cylinder wall outside of an alternating stroke range of the piston 2 for interconnecting the measuring space 4 with the surrounding tested medium 12.

From the determined pressure difference, which corresponds exactly to a pressure loss in the capillary tube 6, or the capillary bundle 6A, and a defined volume of material flow, exact determination of viscosity can be made using known calculations.

A device 8 for measuring displacement-time or speed is part of a control for controlling the piston speed. In addition, this exactly predetermines a starting point and an ending point of a measuring path in the measuring cylinder 3. A signal-processing unit 9, which receives signals indicative of a pressure drop from the pressure gauge 7 and of piston speed from the device 8, indicates or registers the viscosity or transmits the viscosity for controlling a process.

In another embodiment, the viscometer can also be equipped with a temperature-measuring sensor and a device for temperature compensation. Tempering (controlling the temperature of) the measuring space is normally not required, because the entire measuring space is submerged in the tested medium 12, thus it assumes a temperature of the tested medium within a very short period of time.

It is suggested that a reversible rotary electric motor 1 with a worm-gear 20 or other gear drive be used. A linear motor, or an electric motor having a connecting rod or a cam disk can also be used.

The viscometer apparatus of this invention is wear-resistant, not prone to failure, and service-friendly because of its uncomplicated construction, because of the low number of components it has and because it is self-cleaning in operation.

Figure 2:
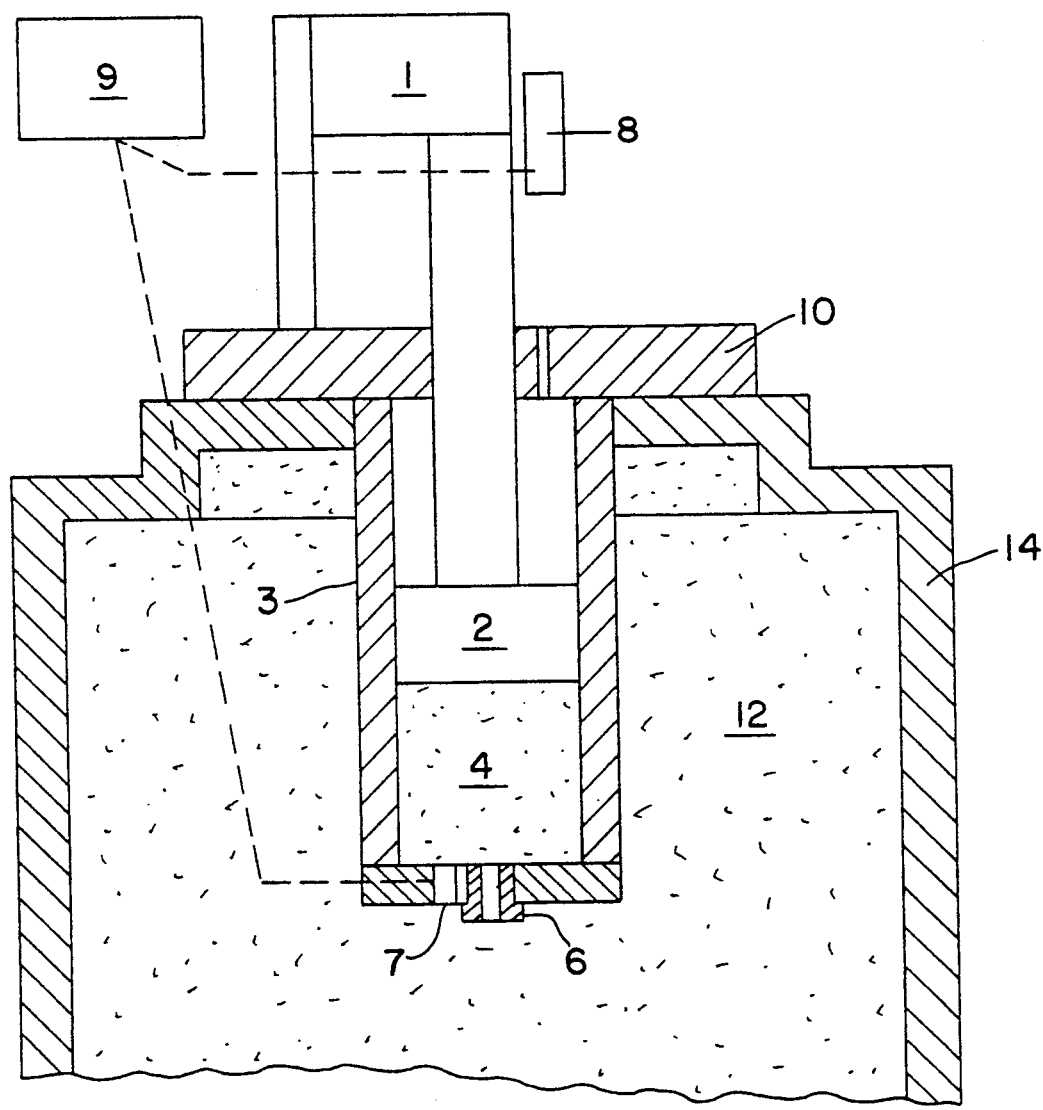
FIG. 2 is a segmented, cross-sectional, schematic side view of a preferred embodiment of the viscometer apparatus of this invention for monitoring and controlling a process in pipes, containers and receptacles.

FIG. 2 depicts a quasi-continuously-measuring capillary viscometer as used in a closed pipe, container or receptacle under positive or negative pressure.

The measuring cylinder 3 of the capillary viscometer is inserted into a prearranged opening of a pipe connection, a container or a receptacle and is pressure-sealed by means of a gasket and a viscometer flange 10. Operation of this viscometer is carried out as is described above for the device of FIG. 1.

The embodiment shown in FIG. 2 is particularly beneficial for controlling viscosity of heating oils for ship engines and incinerators, for controlling fluid-mixing apparatus, and monitoring viscosity during physical and chemical processes in industry, for example a process of boiling sugar.

The described viscometer apparatus of this invention can be used in high pressures and high temperatures and in highly-volatile or explosive arrangements when an appropriate drive is provided. It is also sturdy and not easily prone to failure. It can be used in any position.

Figure 3:
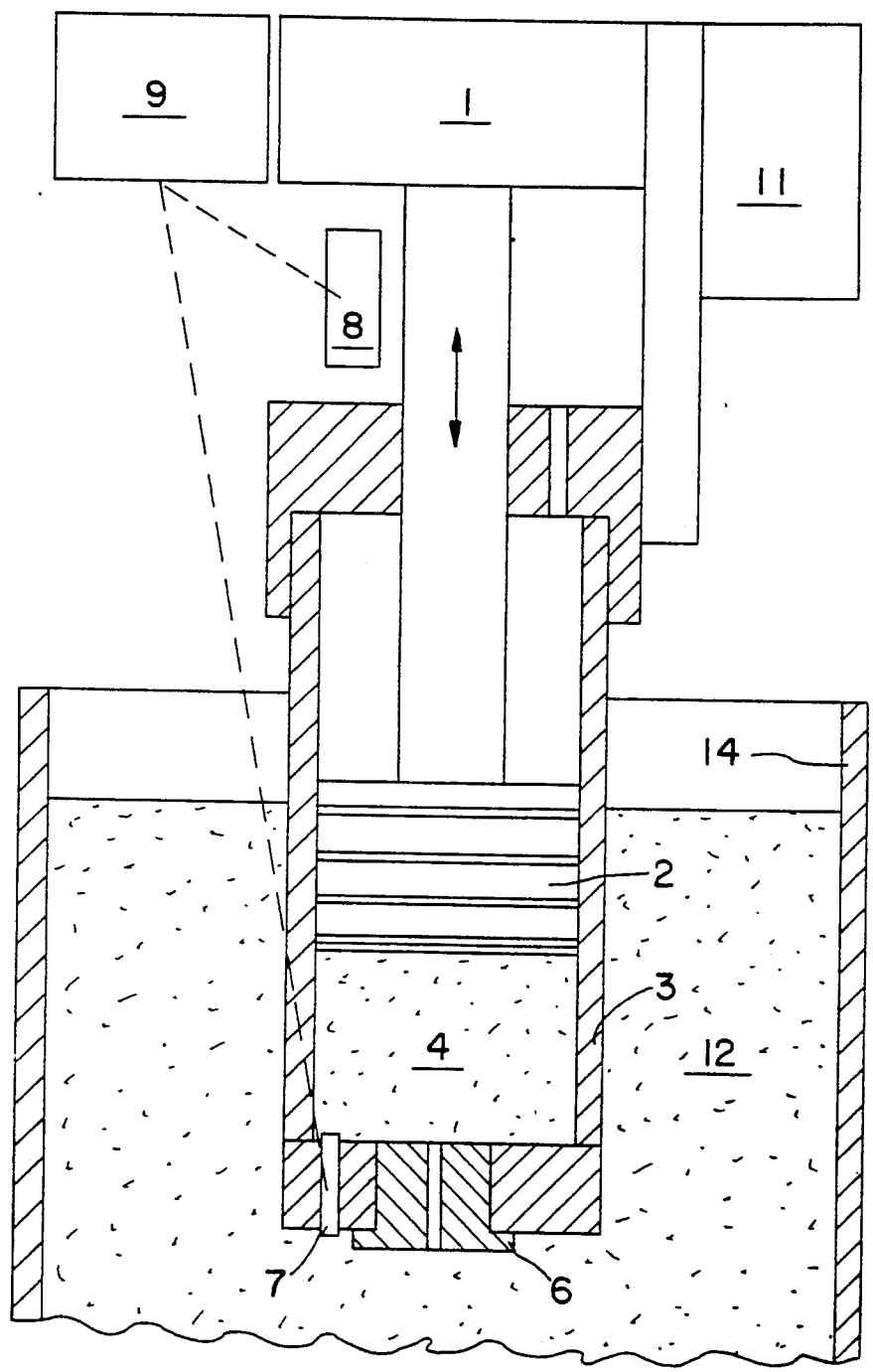
FIG. 3 is a segmented, cross-sectional, schematic side view of another embodiment of the viscometer apparatus of this invention when used as a hand or lab viscometer in a container which is open at its upper end.

FIG. 3 shows the continuously measuring capillary viscometer as used in laboratories or workshops (having a stand or tripod) and as a handheld viscometer (with a handle).

The measuring cylinder 3 of the capillary viscometer is submerged sufficiently deep in the tested medium 12 located in an open container 14 so that during operation the viscometer does not suck in air. The viscometer apparatus can have a capillary tube 6 (or a bundle of tubes) which is arranged preferably near a bottom of the measuring space 4 in a hand-held viscometer. In the embodiment depicted in the drawings, the capillary tube 6 is a separate member from the rest of the measuring cylinder 3 and in one embodiment it can be easily removed from the rest of the cylinder wall. It is beneficial to arrange the differential pressure gauge 7 of the hand viscometer at the bottom of the measuring space. Operation of this viscometer is as is described for the device of FIG. 1.

When operating a hand viscometer, the capillary viscometer is gripped at a handle, the measuring cylinder 3 is submerged in the tested medium and measuring can be carried out as is described above. It is suggested that the measuring cylinder 3 be held in the tested medium long enough for it to assume the temperature of the tested medium, thus ensuring faultless measurements. The measuring space can be emptied by positioning the capillary tube 6 of the operating viscometer above the surface of the tested medium while operating the viscometer. Cleaning of the viscometer is done by submerging the measuring space of the viscometer in a cleansing solution while operating the viscometer and thereafter emptying it.

When operating the viscometer apparatus of this invention in a laboratory or workshop, it is beneficial to position the apparatus with a stand or tripod. In this regard, the measuring cylinder 3 is held submerged sufficiently deep in a container of tested medium. Operation of the apparatus is as described for the device of FIG. 1. It is suggested that the measuring cylinder 3 remain in the tested medium until the measuring cylinder has assumed the temperature of the tested medium. Controlling the temperature of the components involved in the measuring process must be done when measuring small test amounts and for achieving exact measuring results.

The embodiment of the capillary viscometer as a hand viscometer, for use in a lab or workshop, for example, is uncomplicated in construction and handling. It provides fast and reliable results. A hand viscometer can measure directly in a reaction container, thus eliminating the steps of taking a sample and transporting it to a viscometer. Thus, temperature influences are eliminated which may falsify measuring results.

Figure 4:
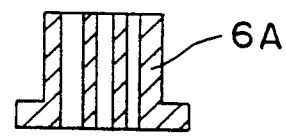
FIG. 4 is a cross-sectional side view of a capillary bundle for use in an alternate embodiment of this invention.

FIG. 4 depicts a capillary bundle 6A of a type which can be used in this invention. In this regard, the capillary bundle 6A has capillary bores therethrough which are stepped, or graduated, to have different diameters. A capillary viscometer apparatus of this invention with a capillary bundle 6A therein can be used to determine crystallization points of mediums which tend to crystallize.

In capillary viscometer, or viscosimeter, apparatus of the prior art, viscosity is measured only in a discontinuous or by-pass manner. The capillary viscometer apparatus of this invention provides uncomplicated and exact measuring of flow characteristics of fluent materials directly in pipes, containers and receptacles under extreme environments and mechanical and climatic stress situations, independently of pressure and flow conditions and of operation positions of the viscometer.

The capillary viscometer of this invention is particularly suitable for use in closed pipes, containers or receptacles which are under pressure, particular negative pressure, in explosion-threatened apparatus and particularly for determination or control of viscosity of fluids which tend to stick. The viscometer of this invention is especially suitable for lab use because of its uncomplicated construction and exchangeability of capillaries or capillary bundles.

The apparatus of this invention has the benefit that the alternating piston movement can be achieved in an uncomplicated manner by means of a reversible electric motor having a worm gear spindle or a gear drive, a linear motor or an electric motor having a connecting crank rod or cam disk.

It is further beneficial that the volume flow, which is pushed or sucked through the capillary tubes or capillary bundle during a measuring process, is only dependent upon a speed of the viscometer piston and geometric measurements of the piston and the measuring cylinder.

It is also beneficial that there are no open surfaces of tested substance in the entire measuring apparatus and therefore no problems with highly volatile fluids or fluids which form a "skin".

Also, it is beneficial that the flow which is forcibly created by the structural arrangement of the measuring apparatus allows continuous exchange of tested medium and provides self-cleaning.

Further, it is a benefit that measured results are not unduly influenced by suspended particles.

It is still another benefit that measured results are independent of a mounting position or attitude of the apparatus.

A further benefit of the apparatus of this invention is that the pressure difference between the measuring space and its surroundings can be measured by known off-the-shelf pressure detectors or sensors.

This invention provides the benefit that the measured pressure difference is in each case the pressure drop required for flow in the capillary tube or capillary bundle, and is independent from pressure variations and flow conditions that are related to the surroundings.

Also, it is beneficial that the measuring process is not limited to sucking or pressing, as compared to prior-art capillary viscometer, but rather measured values are usually determined both ways.

It is another benefit that a differential pressure gauge of this invention can signal excess pressures.

Another beneficial characteristic of this invention is that all parts which come in contact with the tested medium are submerged therein. Thus, controlling the temperature of the viscometer is not required.

While the invention has been particularly shown and described with reference to a preferred embodiment, it will be understood by those of ordinary skill in the art that various changes in form and detail may be made therein without departing from the spirit and scope of the invention.

The embodiments of the invention in which an exclusive property or privilege are claimed are defined as follows:

1. A method for determining flow characteristics of a tested fluent material comprising the steps of:
   inserting a measuring cylinder into the tested fluent materials having at least one capillary opening and a differential pressure gauge arranged in a cylinder wall thereof for interconnecting a measuring space in said measuring cylinder with the tested fluent material;
   moving a piston in the cylinder for pumping said tested fluent material into and out of said cylinder through said capillary opening;
   measuring the differential pressure with said differential pressure gauge between the tested fluent materials in the cylinder and the tested fluent materials outside the cylinder.

2. A method as in claim 1 wherein are included the steps of monitoring motion of the piston and comparing this motion with the differential pressure measured by the differential pressure gauge to determine viscosity of the tested fluent material.

3. A capillary viscometer apparatus for determining flow characteristics of surrounding tested fluent materials in an uncomplicated manner comprising:
   a measuring cylinder having an axially-movable piston therein forming a seal with an interior surface of a cylinder wall for defining a measuring space with said cylinder, a drive means for applying a force to the piston, a displacement-time measuring means for determining the piston movement relative to time, and a signal-processing means for determining viscosity, wherein:
   there is at least one capillary opening and a differential pressure gauge arranged in the cylinder wall outside of a stroke range of said piston for interconnecting said measuring space with the surrounding tested fluent materials, said differential pressure gauge thereby measuring the differential pressure between said measuring space and said surrounding tested fluent materials; and
   said signal-processing means is coupled to said differential pressure gauge for receiving a read-out of a pressure difference between said measuring space and said surrounding tested fluent materials as determined by said differential pressure gauge.

4. A capillary viscometer apparatus as in claim 3 wherein said drive means is a reversible rotary electric motor and wherein is further included a worm gear and wherein power is transmitted to the piston via the worm gear.

5. A capillary viscometer apparatus as in claim 3 wherein a capillary tube defining said at least one capillary opening is detachably attached to said cylinder wall.

6. A capillary viscometer apparatus as in claim 3 wherein said drive means is a reversible rotary electric motor; and
   wherein is further included a gear system and wherein power is transmitted from the motor to the piston via said gear system.

7. A capillary viscometer apparatus as in claim 3 wherein said drive means is a reversible rotary electric motor; and
   wherein is further included a rod and crank system and wherein power is transmitted from said motor to said piston via said rod and crank system.

8. A capillary viscometer apparatus as in claim 3 wherein said drive means is a reversible linear motor.

9. A capillary viscometer apparatus as in claim 3 wherein there are a plurality of capillary openings.

10. A capillary viscometer apparatus as in claim 9 wherein a capillary tube means for defining said plurality of capillary openings is detachably attached to said cylinder wall.

11. A capillary viscometer apparatus as in claim 9, wherein the diameters of said capillary openings are different from one another in steps whereby said capillary viscometer can be used for determining crystallization points of the surrounding tested fluent materials which tend to crystalize.

12. A capillary viscometer apparatus as in claim 3 wherein is further included a container for containing the surrounding tested fluent materials.

* * * * *